United States Patent [19]

Shamos

[11] Patent Number: 4,669,454

[45] Date of Patent: Jun. 2, 1987

[54] PERCUSSING CHIROPRACTIC DEVICE HAVING ADJUSTABLE SPRING FORCE

[75] Inventor: Desmond E. Shamos, Scottsdale, Ariz.

[73] Assignee: Desray, Inc., Phoenix, Ariz.

[21] Appl. No.: 689,436

[22] Filed: Jan. 7, 1985

[51] Int. Cl.[4] ........................ A61F 5/00; A61H 23/00; B25D 1/00

[52] U.S. Cl. ........................................ 128/69; 128/54; 173/120

[58] Field of Search ............... 128/54, 61, 69; 273/69; 173/91, 119, 120, 121

[56] References Cited

U.S. PATENT DOCUMENTS

| | | | |
|---|---|---|---|
| 224,050 | 2/1880 | Snow | 173/120 |
| 1,157,909 | 10/1915 | Teague | 273/69 |
| 2,048,220 | 7/1936 | Redding | 128/69 |
| 2,204,259 | 6/1940 | Schuster | 128/55 |
| 2,470,891 | 5/1949 | Hammers | 173/120 |
| 2,970,592 | 2/1961 | David | 128/69 |
| 3,071,994 | 1/1963 | Swenson | 173/121 |
| 3,706,309 | 12/1972 | Toftness | 128/69 |
| 3,897,061 | 7/1975 | Grattan | 273/69 |
| 4,116,235 | 9/1978 | Fuhr et al. | 128/69 |
| 4,203,446 | 5/1980 | Hofert | 173/119 |
| 4,461,286 | 7/1984 | Sweat | 128/69 |
| 4,498,464 | 2/1985 | Morgan | 128/54 |
| 4,530,584 | 7/1985 | Schmidt | 354/293 |

FOREIGN PATENT DOCUMENTS

| | | | |
|---|---|---|---|
| 23009 | 4/1918 | Denmark | 128/54 |
| 500007 | 5/1919 | France | 173/120 |

*Primary Examiner*—Edgar S. Burr
*Assistant Examiner*—Tonya Eckstine Lamb
*Attorney, Agent, or Firm*—Arnold, White & Durkee

[57] ABSTRACT

A spring-loaded, impact-type chiropractic device especially useful for repositioning a cervical vertebra in the spinal column of a patient. The device includes a tubular casing having an anvil structure at one end and a spring-biased hammer mounted in the tubing. An elongated spindle is connected to the hammer for drawing the hammer away from the anvil into a loaded position in which the spring is compressed. A releasable detent mechanism is provided which holds the hammer in the loaded position or, when released, allows the hammer to strike the anvil. Preferably, the casing includes two telescopically-interfitted tubular portions and one or more hammer-biasing springs; adjustment of the tubular portions relative to each other determines the amount of compression of the springs with the hammer in the loaded position. With the anvil structure adjacent the back of a patient, the device allows the chiropractor to precisely regulate the amount of impacting force transmitted to the patient's back and to accurately direct the blow to reposition a vertebra.

7 Claims, 5 Drawing Figures

PERCUSSING CHIROPRACTIC DEVICE HAVING ADJUSTABLE SPRING FORCE

BACKGROUND TO THE INVENTION

This invention relates to a chiropractic device, and in particular, to a device for use in repositioning spinal vertebrae which have been displaced. One application of a device according to the invention is in the repositioning of the atlas, or first cervical vertabra.

A common spinal complaint arises when the atlas becomes displaced with respect to the axis, or second cervical vertebra, on the odontoid peg of which the atlas is pivotable. A chiropractor will generally treat a complaint of this nature by applying a sharp blow to the atlas to reposition it. At present, there exist no devices suitable for applying an appropriate, controlled impact in these situations.

The present invention seeks to provide such a device.

SUMMARY OF THE INVENTION

For use in applying an impact to a vertebra, the invention provides a device which includes a member having an impacting part for location adjacent the vertebra which is to be impacted, the member defining an anvil, a hammer movable with respect to the member, means biasing the hammer towards the anvil, means for drawing the hammer against the biasing force to a loaded position in which it is spaced from the anvil, and a detent which is operable to hold the hammer in its loaded position and to release the hammer to permit the biasing means to urge the hammer towards the anvil to strike it, with the result that the impacting part of the member applies an impact to the vertebra.

Preferably, the biasing force of the biasing means is adjustable so that an impact of selectively variable magnitude can be applied to the vertebra.

In one form of the invention, the member includes a casing having a projecting impacting part and a blind internal bore in which the hammer is movable, the closed end of the bore providing the anvil.

The biasing means may include a compression spring within the casing and arranged to act between the casing and the hammer. So that the biasing force is adjustable, the casing may be of telescopic configuration so providing an internal space of variable length for accomodating the compression spring.

The detent conveniently includes a latch which is spring loaded to engage the hammer when it is withdrawn to its loaded position and which is movable against the spring-loading force to release the hammer for biased movement from its loaded position towards the anvil.

DESCRIPTION OF THE PREFERRED EMBODIMENT

Figures 1, 2, 3, 4, 5:
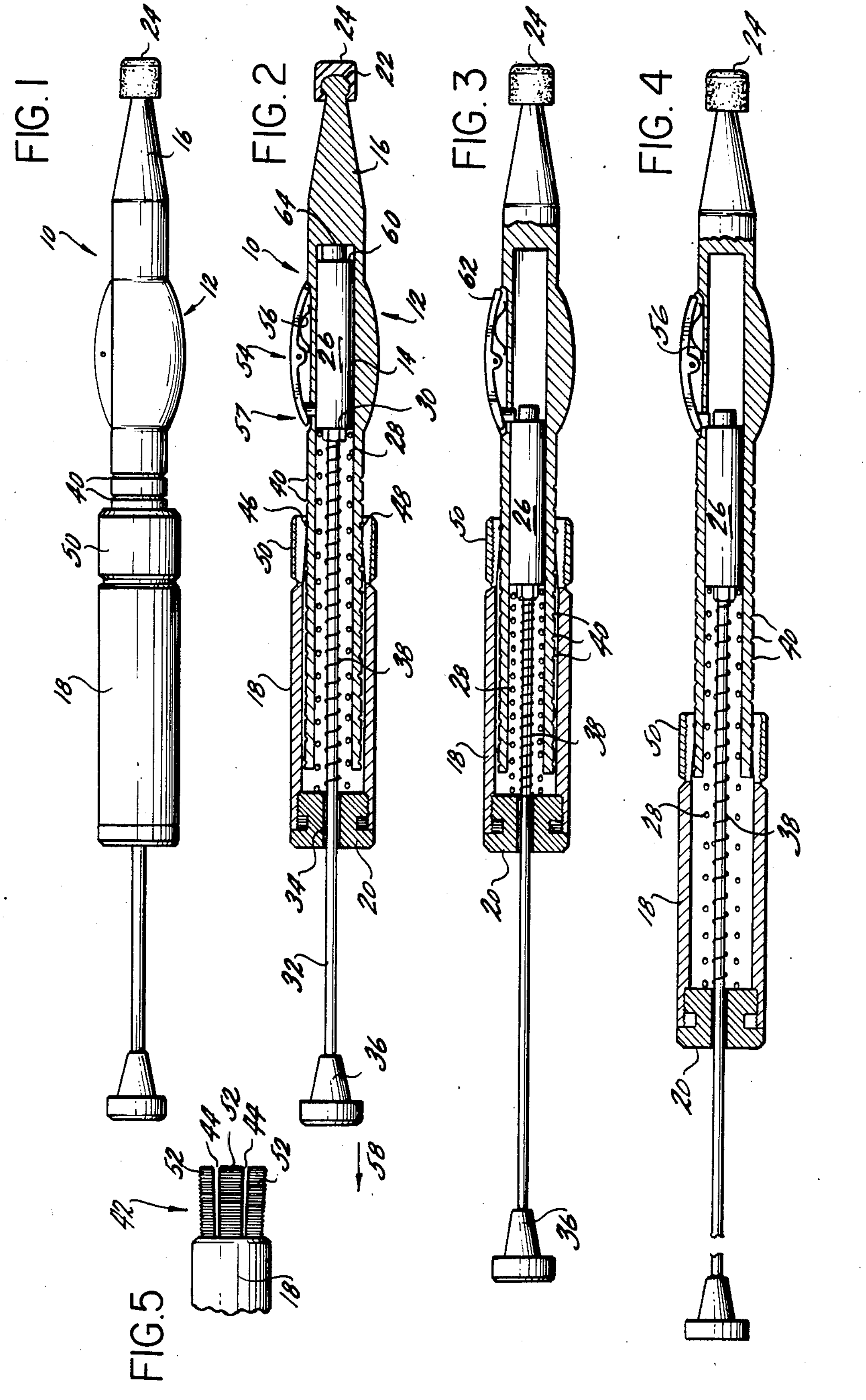
FIG. 1 shows a side view of a device according to the invention, in a first unloaded state.
FIG. 2 shows a cross-sectional view of the device in the unloaded first state of FIG. 1.
FIG. 3 shows a cross-sectional view of the device in the state of FIG. 1, but loaded.
FIG. 4 shows a cross-section of the same device in a second state, the device being loaded.
FIG. 5 shows a view of the forward end of the rear casing portion of the device.

The illustrated device has a casing 10 which includes a forward portion 12 formed with a blind bore 14 and with a forwardly projecting nose 16, a hollow cylindrical rear portion 18 arranged telescopically with respect to the forward portion, and a cap 20 threaded into the rear end of the portion 18.

The bulbous end 22 of the nose 16 is housed within a rubber or soft plastic cap 24.

A hammer 26 is slidable within the blind bore 14 and a robust helical compression spring 28 is arranged to act between the cap 20 and the rear end 30 of the hammer to which is attached a spindle 32 extending rearwardly through an axial openng 34 in the cap and terminating at a knob 36. A further helical compression spring 38, less robust than the spring 28, is also arranged to act between the cap 20 and the end 30 of the hammer.

The external surface of the casing portion 12 towards its rear end is formed with a series of spaced annular grooves 40, each having the cross-section of a semi-circle. The forward end of the casing portion 18 is provided by an externally threaded spigot 42 (see FIG. 5) which has a series of narrow, spaced, longitudinal slots 44 extending rearwardly from its forward edge. The spigot 42 has an internal annular groove 46, also of semi-circular cross-section, a short distance from its forward end, the groove accomodating a circlip 48 of circular cross-section. That part of the circlip 48 which projects radially inwardly from the groove 46 can locate in a selected one of the grooves 40. There is an internally threaded sleeve 50 which, when run up tightly on the threads of the spigot 42, draws together the portions 52 of the spigot between the slots 44 to clamp the spigot firmly onto the casing portion 12 with the circlip 48 located in the selected groove 40.

Pinned to the casing portion 12 at an outwardly bulging section thereof near to the nose 16, there is a latch 54 which is biased by a spring 56 in the direction of the arrow 57.

In use, the sleeve 50 is loosened off, and the casing portion 18 is telescoped relative to the casing portion 12 to the desired position. The sleeve 50 is then run up tightly on the spigot 42 to clamp the portion 18 to the portion 12 and define the length of the space for accomodation by the springs 28 and 38. Next, the knob 36 is gripped, and pulled to rear, in the direction of the arrow 58, to load the device.

As soon as a shoulder 60 on the hammer passes the rear end of the latch 54, the latch is pivoted by the spring to engage in front of the shoulder and hold the hammer against forward motion under the influence of the springs 28 and 38. If the forward end 62 of the latch is now depressed, the latch will clear the shoulder and the hammer will be thrown forwardly to strike the anvil provided by the closed end 64 of the blind bore 14. The impact is transmitted through the nose 16 to the cap 24. The impact so transmitted can be used to reposition a dislocated vertebra if the cap 24 is held against the skin next to the vertebra in question before the latch end 62 is depressed.

Each of the grooves 40 are numbered, to enable a practitioner to gauge accurately the impact which will be provided when the device is used. In the case of FIGS. 1 to 3, the circlip is located in groove no. 3, with the result that the spring 28, which provides the major forward thrust, is greatly compressed before loading, and even more so after loading. In FIG. 4, the circlip is located in groove no. 12, with the result that the spring 28 is not compressed to the same extent as in FIGS. 1 to 3. The impact provided by the device with this telescopic setting is therefore not so great as with the setting of FIGS. 1 to 3. The practitioner is therefore able to use the device to apply a closely controlled impact to the affected area to achieve the result which he seeks.

I claim:

1. A chiropractic device adapted for striking a blow to a cervical vertebra of a patient, comprising:

an elongated, tubular casing having a vertebra engaging nose at the forward end thereof;

hammer means slidably disposed within the casing between a first position, in which a portion of the hammer is proximate the nose and a second position with the hammer remote from the nose;

spring means operably coupled to the hammer and casing for biasing the hammer towards the first position;

detent means for releasably holding the hammer in the second position and operable for releasing the hammer to allow the hammer to strike the nose;

the casing including first and second, tubular, telescopic portions and means for adjustably coupling said portions to vary the longitudinal dimension of the casing to vary the bias force of the spring means;

a plurality of longitudinally spaced, circumscribing grooves along the outer surface of the innermost telescopic portion;

a compressible spigot at one end of the outermost portion adjacent said grooves and having a radially-inward extending clip; and a sleeve engaging the spigot operable for inwardly compressing the spigot and inwardly projecting the clip to project the clip into one of the grooves to telescopically lock said portions relative to each other.

2. A chiropractic device comprising:

a support member having an elongated tubular casing including a tubular forward portion telescopically interfitted with a tubular rear portion, said support member having an impacting nose and an anvil, the impacting nose being adapted for positioning adjacent a vertebra of a patient;

a hammer operably disposed within and coupled to the support member for slidable movement along the member between a first position, in which the hammer abuts the anvil, and a second position with the hammer remote from the anvil;

biasing means operably disposed within and coupled to the hammer for biasing the hammer from the second position towards the first position;

releasable detent mechanism for holding the hammer in the second position, the mechanism being operable for releasing the hammer to allow the hammer to strike the anvil and transmit a vertebra moving force to the impacting nose; and releasable coupling means for adjustably connecting the forward and rear portions for longitudinal displacement relative to each other, said coupling means comprising a plurality of longitudinally spaced, circumscribing grooves along the outer surface of the forward portion, a compressible spigot at one end of the rear portion and having a radially-inward extending clip, a sleeve positionable on the spigot for inwardly compressing the spigot and inwardly projecting the clip, such that with the sleeve removed from the spigot the front and rear portions are telescopically adjustable and with one of the grooves disposed adjacent the clip, positioning the sleeve on the spigot compresses the spigot and projects the clip into the one groove to lock the front and rear portions relative each other.

3. The chiropractic device according to claim 2, said casing having the anvil connected at one end thereof and a cap coupled at the other end.

4. The chiropractic device according to claim 3, said biasing means comprising one or more helical springs mounted in the casing between the hammer and the cap.

5. The chiropractic device according to claim 4, including an elongated spindle connected to the hammer and extending through the cap, the spindle being longitudinally shiftable for positioning the hammer in the second position with the spring compressed.

6. The chiropractic device according to claim 2, said biasing means including one or more springs received in the tubular rear portion whereby the positioning of the front and rear portions relative to each other determines the amount of biasing potential force available.

7. The chiropractic device according to claim 2, said detent mechanism being coupled to the casing and pivotable for releasably engaging the hammer when the hammer is in the second position.

* * * * *